United States Patent [19]

Zeicher et al.

[11] Patent Number: 5,002,753
[45] Date of Patent: Mar. 26, 1991

[54] SPECIFIC LIGANDS FOR ESTROGEN AND PROGESTAGEN STEROID HORMONE RECEPTORS, APPLICATION AND INTERMEDIATE SYNTHESIS PRODUCTS

[75] Inventors: Marc Zeicher, Brussels; Jacques Quivy, Louvain la Neuve, both of Belgium

[73] Assignee: IRE-Celltarg S.A., Fleurus, Belgium

[21] Appl. No.: 423,141

[22] Filed: Oct. 18, 1989

[30] Foreign Application Priority Data

Oct. 19, 1988 [FR] France ............................... 88 13737

[51] Int. Cl.$^5$ .............................................. A61K 43/00
[52] U.S. Cl. ................................................... 424/1.1
[58] Field of Search ....................... 552/539; 424/1, 1.1

[56] References Cited

FOREIGN PATENT DOCUMENTS 0137434 4/1985 European Pat. Off. .
0169511 1/1986 European Pat. Off. .
2268528 11/1975 France .
2613937 10/1988 France .

OTHER PUBLICATIONS

Ratajczak et al., *Steroids* (1981), 38:537-555.
Chemical Abstracts, vol. III (1989), #187,600w; Quivy et al.

*Primary Examiner*—Stanley J. Friedman
*Assistant Examiner*—Theodore J. Criares
*Attorney, Agent, or Firm*—Bertram I. Rowland; Richard L. Neeley

[57] ABSTRACT

The present invention relates to specific ligands for estrogen or progestagen steroid hormone receptors which have the formula

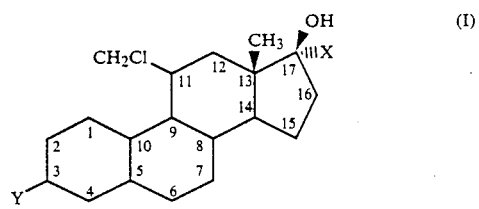

in which X denotes a vinyl group substituted by a radioactive or nonradioactive halogen on the double bond according to a Z isomerism, and Y denotes either a hydroxyl group, in which case the ring to which it is attached is an aromatic ring, or a ketone functional group, in which case it is conjugated with a double bond at $C_4$–$C_5$.

An application of the ligands according to the invention is the targeted therapy and/or medical imagery, especially of cancer. However, these ligands can also be employed in the quantitative determination of said hormone receptors.

However, the labeled ligands according to the invention are of very particular interest in the case of the targeted radiotherapy of cancer.

14 Claims, 1 Drawing Sheet

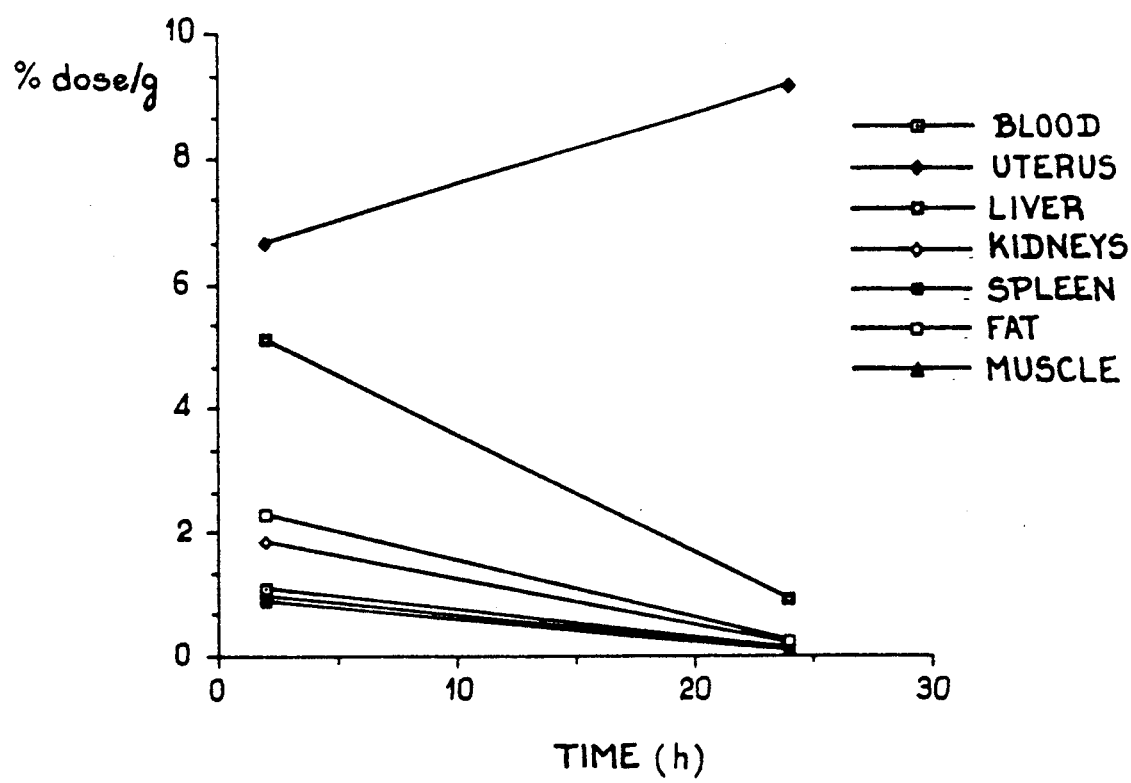

SPECIFIC LIGANDS FOR ESTROGEN AND PROGESTAGEN STEROID HORMONE RECEPTORS, APPLICATION AND INTERMEDIATE SYNTHESIS PRODUCTS

The present invention relates to new specific steroid ligands of estrogen or progestagen hormone receptors.

An application of the ligands according to the invention is the targeted therapy and/or medical imagery, especially of cancer. However, these ligands can also be employed in the quantitative estimation of the said hormone receptors.

An objective of the present invention is to propose steroid hormone analogs exhibiting a high affinity for the hormone receptor and binding seemingly irreversibly to the receptor with a view to improving the proportion of analogs which are fixed.

Another objective of the present invention is to make the halogenated derivatives of these analogs stable in the extracellular medium, especially in plasma, as in the cytoplasm, while retaining a high affinity for the hormone receptor.

When subjected to these derivatives, all the cells containing hormone receptors, be they malignant or healthy, can be the subject of an increase in cytotoxicity.

However, an improved selectivity is observed nevertheless, since in the chemotherapy treatments of conventional cancer the healthy estrogen target tissues either have a low rate of cell proliferation, or are not essential to life. The same applies in the case of the progestagen receptors.

The subject matter of the present invention is therefore specific ligands for estrogen or progestagen steroid hormone receptors, which have the formula

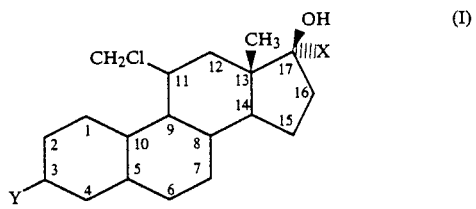

in which
X denotes a vinyl group substituted by a radioactive or nonradioactive halogen on the double bond according to a Z isomerism, and
Y denotes either a hydroxyl group, in which case the site to which it is attached is an aromatic ring, or a ketone functional group, in which case it is conjugated with a double bond at $C_4$–$C_5$.

The characteristic features of these products of formula I are that they comprise, in particular:
a: a hydroxyl or ketone functional group in the $C_3$ position,
b: a beta-oriented chloromethyl functional group in the $C_{11}$ position,
c: an alpha-oriented vinyl functional group in the $C_{17}$ position, and, either
$d^1$: any nonradioactive halogen, namely iodine, fluorine, chlorine or bromine, which halogen is substituted on the double bond of the vinyl group, according to a Z isomerism, or
$d^2$: a radioactive isotope of a halogen chosen from fluorine, iodine, bromine and astatine, substituted on the double bond of the vinyl group according to a Z isomerism, especially the isotopes $^{18}F$, $^{80m}Br$, $^{211}At$, $^{125}I$ and $^{123}I$.

The functional groups in positions $C_3$ and $C_{17}$ give these ligands a high affinity for the hormone receptors for which they are intended, namely especially estrogen or progestagen receptors.

The 11beta-chloromethyl functional group ensures a seemingly "irreversible" bond between the steroid and the receptor; what is involved, in fact, is rather a very high affinity for the receptor.

The formation of the seemingly "irreversible" bond between the steroid and the receptor improves the stability of the complex and increases its concentration in the nucleus.

The bonding sites of estrogen and progestagen hormones are homologous with amino acid sequences, which accounts for their common behavior with regard to the irreversible bonding between the receptor and the steroid in the presence of an 11beta-chloromethyl functional group.

These derivatives have a vinyl functional group at $C_{17}$ alpha to the $C_{17}$ position, and this gives them a metabolic resistance and a reduced bonding to the plasmatic bonding proteins.

According to the invention, the halogen is situated on the double bond of the alpha-oriented vinyl in the $C_{17}$ position according to a Z isomerism. These ligands are specific for the estrogen and progestagen receptors. This position has the advantage of exhibiting a high stability.

Ligands which may be mentioned in particular according to a first alternative form are those in which the functional group at $C_3$ is a hydroxyl group, the ring to which it is attached being an aromatic ring. These ligands are more specific for the estrogen receptors.

Ligands which may also be mentioned according to a second alternative form of the invention are ligands in which the functional group in the $C_3$ position is a ketone functional group conjugated with a double bond at $C_4$–$C_5$. These ligands are specific more particularly for the progestagen receptors.

Among the ligands which are more specific for the estrogen receptors, mentioned above, there may be mentioned the 11beta-chloromethyl-17alpha-halovinylestradiols.

Among the ligands according to the invention which are the most specific for the progestagen receptors there may be mentioned in particular the 11beta-chloromethyl-17alpha-halo-17beta-hydroxy-19-nor-4-androsten-3-ones.

In the ligands according to the invention, the halogen may be nonradioactive; the ligands will then be useful in quantitive determinations of steroid hormone receptors and for any therapeutic use where a powerful estrogenic or progestative effect is required.

The estrogen derivatives according to the invention can also be employed in the induction of receptors of progestatives with a view to the targeted therapy of cancer using radioactive progestatives.

When the halogen is radioactive the ligands can be used both in medical imagery and in targeted radiotherapy, particularly of cancer, but can also be used as reactants in the case of quantitative determination of steroid hormone receptors.

However, the labelled ligands according to the invention are of a particular interest in the case of targeted cancer radiotherapy.

In fact, steroid hormones bind with a high affinity to the cytoplasmic protein receptors of the target cells and, after bonding, undergo a translocation in the cell nucleus and activate the transcription of the portions of the genome relating to the specific physiological effect of the hormone. Given the passage of the steroid-receptor complex close to the DNA, a radioactive halogen carried by the steroid will be able to severely damage the DNA and to have a lethal effect on the target cell.

Now, a certain number of cancers exhibit a high concentration of specific receptors either for estrogens or for progestagens. The cancers involved are especially those of the breast, of the uterus, of the ovary and of the prostate. For example, 65% of breast cancers exhibit detectable levels of estrogen receptors (from 5,000 to 50,000 molecules of receptors per cell).

A radioactive halogen attached to the steroid will permit the specific destruction of the cancerous cells. In addition, some will enable the tumor to be visualized by radioimagery. In fact, these ligands then form agents for directing an additional active element, which is their radionuclide.

In the case of intracellular fixation sites such as the hormone receptors, hormone analogs exhibiting a high affinity for the receptor and a low affinity for the plasmatic bonding proteins will be the most suitable directing agents.

The use of radioisotopes which decay emitting Auger electrons is very auspicious in targeted radiotherapy. Due to the short range of the Auger electrons, the efficiency of such radioisotopes, insofar as the cell inactivity is concerned, is completely lost when they are not bonded or, at the outside, at a distance of a few atoms from the DNA.

According to the invention, it has been found that iodine 123, which has a half-life of 13.21 hours and produces about twenty Auger electrons per disintegration, has a half-life which is sufficiently short not to expose the patient unnecessarily to doses of radioactivity for an extended period, but also sufficiently long to permit the synthesis of radiopharmaceutical products and their shipment to the treatment centers situated far from the production cyclotron, bearing in mind the fact that provision must be made for up to 48 hours, travel and 24 hours' treatment.

Ligands which are more particularly useful for targeted radiotherapy will therefore comprise the isotope $^{123}$I as radioactive iodine. However, bromine $^{80m}$Br or else iodine $^{125}$I will also be acceptable in radiotherapy as Auger electron emitters.

Directed in this way, the radioactive halogens exhibit a high cytotoxic activity insofar as they are brought close to the DNA, in which they induce scissions in the double helix.

Astatine $^{211}$At, an alpha-ray emitter whose energy is absorbed over a distance of approximately 50 microns, which corresponds to a few cell diameters, can be employed for a radiotherapy which permits killing also the cells neighboring the cells containing the steroid receptors.

Ligands which are more particularly useful for medical imagery, especially of cancer, will carry iodine $^{123}$I or fluorine $^{18}$F.

Ligands which are more particularly useful for the quantitative estimation of hormone receptors will carry an iodine $^{125}$I.

According to the present invention, it has been found that the Z isomerism of the said halovinyl functional group, especially the Z isomerism of the 17alphahalovinyl functional group and in particular the Z isomerism of the 17alpha-iodovinyl functional group is preferable, because it imparts a better accumulation to the ligands according to the invention with estrogen or progestagen activity than the corresponding E isomerism in the receptor-rich tumors.

The Z isomers are less hydrophobic than the E isomers and have greater affinity for the estrogen or progestagen receptors. In addition, a lower hydrophobicity reduces the nonspecific fixation in the fatty tissue, which is a limiting factor for the use of steroid hormones in imagery.

Finally, another subject of the present invention, as a new product usable especially as an intermediate product for the synthesis of estrogen and progestagen analogs according to the invention, is derivatives of formula (I) in which a tributylstannyl group is substituted on the double bond of the vinyl group attached at $C_{17}$; according to Z isomerism, instead of the halogen.

A process forming a subject of the invention consists in obtaining the halogenated derivative from this tributylstannyl intermediate derivative.

Other features and advantages of the present invention will become apparent in the light of the description which is to follow.

The description which is to follow is given with reference to FIG. 1, which shows the accumulation of the Z isomer of the 16' derivative (Example 1) in various tissues of ovarectomized BDF1mice as a function of time.

EXAMPLE 1

Ligands Specific for the Estrogen Receptor

Scheme I hereinafter reproduces a synthesis of the 11beta-chloromethyl-17alpha-iodovinylestradiol ligand.

Stage 1 consists of a preparation of the $\Delta^1$adrenosterone-17-ethylene ketal from $\Delta^1$-adrenosterone (1').

25 g of $\Delta^1$-adrenosterone (84 mM) are added with vigorous stirring to a mixture of 500 ml of benzene, 25 ml of ethylene glycol (approximately 420 mM) and 1 g of para-toluenesulfonic acid.

The mixture is refluxed for 4 hours in a DeanStark apparatus.

The reaction mixture is extracted with 200 ml of water containing 1 g of bicarbonate and then with water saturated with salt, and is dried and then evaporated down.

A yellow mass is obtained, which is washed with 200 ml of warm isopropyl ether.

The white crystals are filtered off and then dried at 60° C; a mass of ±26 g is obtained.

Stage 2 consists of the preparation of 11$\beta$-hydroxy-17-ethylene ketal androsta-1,4-dien-3,17-dione (2').

340 g of (1') (88 mM) are added under nitrogen to a suspension of 50 g (±200 mM) in 400 ml of tetrahydrofuran.

After 24 hours' reaction at ordinary temperature, 100 ml of ether, followed by 40 ml of 1N NaOH, followed by 25 g of anhydrous sodium sulfate. Stirring is continued overnight.

The mixture is filtered and the filtrate is then evaporated down under vacuum.

The solid mass obtained is washed with 200 ml of warm diisopropyl ether.

After filtration and drying, 24 g of a white powder (70.6 mM) are obtained.

Stage 3 consists of the preparation of 3,11β-dihydroxy-estra-1,3,5(10)-trien-17-one-17-ethylene ketal (3').

A mixture of 3 g of oil-coated lithium (approximately 0.4 M), 25 g of biphenyl (0.16 M) and of diphenylmethane (0.08 M) in 360 ml of tetrahydrofuran is refluxed under a nitrogen atmosphere for 1 hour.

The dark-blue reaction mixture, to which 20.7 g of (2') are added, is refluxed again for 30 minutes.

After cooling, 8 ml of methane are added, followed by 100 ml of water, and the solvent is evaporated down under vacuum.

After redissolving the remaining mass in ether, the product formed is extracted with 300 ml of 5% KOH, which is reacidified with acetic acid (12 ml).

The yellow precipitate is re-extracted with ethyl acetate. After evaporating the solvent, the product is redissolved in 15 ml of a warm mixture of acetone and diisopropyl ether.

After two crystallizations, 10.5 g of product are obtained.

The corrected melting point is: 191.1° C.

Stage 4 consists of the preparation of 3-benzyloxy-11β-hydroxyestra-1,3,5(10)-trien-17-one-17-ethylene ketal (4,).

A mixture of 10.3 g of (3') (30 mM), 5,2 g of ground anhydrous $K_2CO_3$ and 100 ml of methyl ethyl ketone is refluxed for 1 hour with vigorous stirring.

5.4 ml (45 mM) of benzyl bromide are then added and refluxing is maintained for 48 hours.

After extraction, 15 g of a yellowish oil are obtained. This oil is used as such in the synthesis of (5').

Stage 5 consists of the preparation of 3-benzyloxyestra-1,3,5(10)-trien-11,17-one-17-ethylene ketal (5').

30 mM of crude (4') (13 g) dissolved in 50 ml of dry methylene chloride are added in one lot to the mixture of 13 g of pyridinium chlorochromate in suspension in 200 ml of dry methylene chloride.

After 3 hours' stirring at ambient temperature, 250 ml of ether are added, which causes a black mass to precipitate.

The solvents are decanted and the insoluble material is washed with 4 50-ml portions of the $CH_2Cl_2$/ether v/v mixture.

The organic phase is percolated on a florisa column, and is then evaporated down.

After purification on silica 9.6 g of a yellowish oil are obtained.

Stage 6 is the preparation of 3-benzyloxy-11-hydroxy-11-methyltrimethylsilaneestra-1,3,5(10)-trien-17-one 17-ketal (6')

8.6 g of (5') dissolved in 100 ml of ether (20 mM) are added rapidly to 165 ml of a 1 M solution of methyltrimethylsilylmagnesium chloride.

The mixture is heated under reflux for 5 hours and is then decomposed and extracted.

The crude product is purified on silica; 5.7 g of a viscous oil which crystallizes are obtained.

Stage 7 is the preparation of 3-benzyloxy-11-methylene-1,3,5(10)-estratrien-17-one (7').

After addition of 0.5 ml of concentrated HCl, a solution of 5.2 g of (6') (10 mM) in 50 ml of acetone is stirred for 2 hours at ambient temperature. The reaction mixture is neutralized with $HCO_3^-$, concentrated under vacuum and extracted with $CH_2Cl_2$.

The crude product is recrystallized from acetone. 3.4 g of yellowish crystals are obtained. The corrected melting point is: 168.1° C.

Stage 8 consists of the preparation of 3-benzyloxy-11-methylene-1,3,5(10)-estratrien-17-one 17-ketal (8').

A solution of 3 g of (7'), 7 mM, 100 ml of benzene, 3 ml of diethylene glycol and 150 mg of paratoluenesulfonic acid is refluxed in a Dean-Stark apparatus for 4 hours.

Extraction followed by solvent evaporation yields 3.3 g of a white oil which is employed as such.

Stage 9 consists of the preparation of 3-benzyloxy-11-hydroxymethyl-1,3,5(10)-estratrien-17-one 17ketal (9').

0.5 ml of the borane-oxathiane complex (±6 mM) are added to a solution of 2.84 g of (8') (±6 mM) in 20 ml of dry THF. After one hour's reaction, 6 ml of ethanol are added, followed by 4 ml of 3 M NaOH (±12 mM), and lastly 10 ml of 30% $H_2O_2$ (±12 mM). After one night at ambient temperature, the reaction mixture is extracted with $CH_2C_2$. A white oil which crystallizes rapidly is obtained (weight: 2.4 g).

Stage 10 consists of the preparation of 3-benzyloxy-11-chloromethyl-1,3,5(10)-estratrien-17-one (10').

The suspension formed in 30 ml of THF by the reaction of 2.1 g of triphenylphosphine (8 mM) and 1.07 g (±8 mM) of N-chlorosuccinimide is added to a solution of 2 g of (9') of approximately 4 mM in 20 ml of tetrahydrofuran.

The mixture, which becomes clear after about 1 hour, is left at ambient temperature overnight. The THF is evaporated off under vacuum, the crude residue is redissolved in 50 ml of acetone, to which 0.5 ml of concentrated HCl are added. The mixture is left stirred for 2 hours. Extraction followed by purification on silica yields white crystals amounting to 1.02 g.

M.s. (FAB) 435 (M+1).

Stage 11 consists of the preparation of 3-benzyloxy-11-chloromethyl-1,3,5(10)-estratrien-17α-ethynyl17β-hydroxy (11').

400 mg (±4 mM) of the lithium acetylide-ethylenediamine complex are added to a solution of 0.93 g of (10') (about 2 mM) in 10 ml of tetrahydrofuran. After 4 hours' reaction, 400 mg of reactant are added again. The reaction is allowed to proceed overnight at ambient temperature.

Extraction with $CH_2Cl_2$ followed by purification on silica gives us approximately 500 mg (1.02 mM) of a slightly yellowish solid.

Stage 12 consists of the preparation of 11chloromethyl-3,17β-dihydroxy-17α-ethynyl-1,3,5(10)estratriene (12').

440 mg of (11') 0.9 mM are dissolved in 20 ml of cold methylene chloride.

4.5 ml (4.5 mM) of a 1 M solution of the $BF_3/(CH_3)_2S$ complex are then added.

The reaction mixture is stirred cold for 45 minutes.

Extraction followed by purification on silica gives us an oil which crystallizes, with a mass of approximately 150 mg (0.375 mM).

Stage 13 consists of the preparation of the derivative (E)-11-chloromethyl-3,17β-dihydroxy-17α-(2tributylstannylvinyl)-1,3,5(10)-estratriene (13').

150 μl of tributyltin hydride (about 0.55 mM) and 5 mg of AIBN (about 0.03 mM) are added under $N_2$ to a solution of 50 mg of (12'): 0.15 mM in 1 ml of THF.

The tube is closed hermetically and then agitated in an oil bath at 70° C. for 1 hour.

The reaction mixture is extracted with an ethyl acetate/water mixture.

The crude oil is purified using silica; 55 mg of a white oil are obtained.

Stage 14 consists of the preparation of the derivative (E)-11-chloromethyl-3,17β-dihydroxy-17α-(2-iodovinyl)-1,3,5(10)-estratriene (14′).

A 0.1 mM iodine solution in $CH_2Cl_2$ is added dropwise to a solution of 32 mg of (13′) (0.05 mM) in 3 ml of $CH_2Cl_2$ until the pink color persists.

After 30 minutes, about 10 ml of $H_2O$ are added with a little $NaHSO_3$, and extraction with $Et_2O$ is carried out.

The crude product is then purified on silica; 20 g of white crystals are obtained, amounting to a mass of 20 mg.

Spectroscopic data: NMR($CDCl_3$, $(CD_3)_2SO$) S 1.1 (S,13$CH_3$), 3.45 (m, C$\underline{H}$HCl), 3.62 (dd, CH$\underline{H}$Cl), 6.27 (d, C$\underline{H}$=CHI, J=14 Hz), 6.53 (d, H(4)), 6.66 (dd, H(2)), 6.81 (d, CH=C$\underline{H}$I, J=14 Hz), 7.03 (d, H(1)).

Labeling starting with the tributyltin derivative

50 μl of a solution of the derivative (E)-17alpha-tributyltinvinyl-11beta-chloromethylestradiol (13′ in the scheme 1 bis) in absolute ethanol at a concentration of 1 mg/ml are added to 1 mCi of $Na^{123}I$ (10 μl in $H_2O$, pH 7–11) contained in an approximately 500-μl screw-cap tube. 10 μl of a solution of chloramine T at a concentration of 1 mg/ml are added and agitated vigorously for 15 seconds. Next, 10 μl of a solution of $Na_2S_2O_5$ at a concentration of 2 mg/ml and 200 μl of pH 7.4 phosphate buffer are added. The mixture is transferred onto cartridge SPE C18 (1 ML, Baker) and the steroid is eluted with 1 ml of ethanol. After evaporation of the solvent, the labelled steroid is purified on an HPCl μ Bondapak C18 column with a mobile phase of 50% $H_2O$ and 50% of acetonitrile. The retention time is of the order of 17 minutes.

C-Synthesis of the Z Isomer (Scheme 1 Bis)

Stage 15 consists of the preparation of the derivative (Z)-11-chloromethyl-3,17beta-dihydroxy-17alpha-(2-tributylstannylvinyl)-1,3,5(10)-estratriene (15′).

105 mg (0.3 mmol) of derivative (12′), 0.6 ml of HMPTA (hexamethylphosphortriamide) and 0.3 ml of tributyltin hydride (0.6 mmol) are placed in a screw-top tube, under argon.

The mixture is reacted for 60 hours with vigorous agitation in an oil bath at 70° C. Next, 5 ml of water are poured in and an extraction with 3×5 ml of ethyl acetate is carried out. After evaporation of the solvent, a whitish oil is obtained, which is purified on silica using a mixture of $CH_2Cl_2$ and $CH_3OH$. 40 mg of a white oil (23%) are obtained; 75% of the product is recovered. TLC: 2% $CH_3OH$ in $CH_2Cl_2$ R$_f$: 0.58.

Stage 16 consists of the preparation of the derivative (Z)-11beta-chloromethyl-3,17beta-dihydroxy17alpha-(2-iodovinyl)-1,3,5(10)-estratriene (16′).

30 mg of the derivative (15′) are dissolved in 10 ml of $CH_2Cl_2$; a 1 M solution of $I_2$ in $CH_2Cl_2$ is added thereto until a pink color persists. The excess $I_2$ is neutralized with an $H_2O$ solution of bisulfite. After extraction, the crude product is collected and is purified by chromatography on silica (98% $CH_2Cl_2$ 2% ether). Approximately 15 mg of white crystals are obtained.

TLC: 2% $CH_3OH$ in $CH_2Cl_2$

R$_f$: 0.4

NMR: ($CDCl_3°$ /1.1 (s, 13$CH_3$), 3.45 (m, C$\underline{H}$HCl), 3.58 (dd, CH$\underline{H}$Cl), 6.38 (d, C$\underline{H}$=CHI, J=8Hz), 6.55 (d, H(4)), 6.65 (dd, H(2)), 6.85 (d, CH=C$\underline{H}$I, J=8Hz), 7.05 (d, (H(1)).

Labeling of the derivative (16′) with $^{125}I$ or $^{123}I$ and stability of the radioactive solution Example with $Na^{125}I$ The method is the same as for the labelling of (14′).

The starting material is the derivative (15′).

The HPLC separation conditions are different: the mobile phase is 60% ethanol in water, the flow rate is 1 ml/min, the final product is collected at 12 minutes. The labeled product is kept as such in the column eluate (60% ethanol). In these conditions, it is stable for at least 12 days at −20° C. (deiodination less than 2%).

Hydrophobicity

The Z isomer (16′) is less hydrophobic than the E isomer (14′) when reference is made to a hydrophobicity index based on the retention time of these 2 products in HPLC (reverse phase). Thus, at a flow rate of 1 ml/min of 60 M ethanol in $H_2O$ on a microBondapack C18 column, the Z isomer (16′) has a retention time of 12.1 minutes and the E isomer (14′) of 14.3 minutes.

A lower hydrophobicity reduces the nonspecific fixation in the fatty tissue, a fixation which is a limiting factor in the case of the use of steroid hormones in imagery.

SCHEME 1

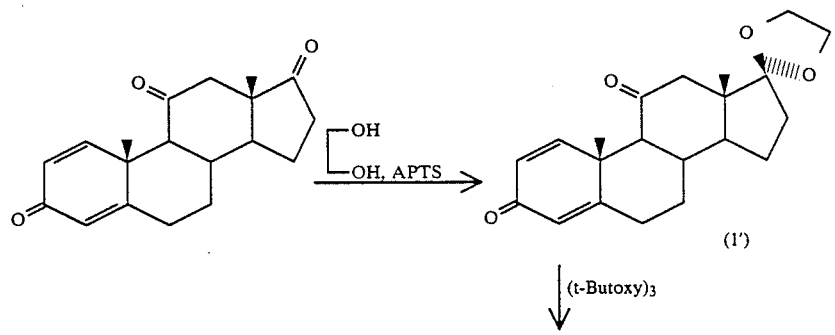

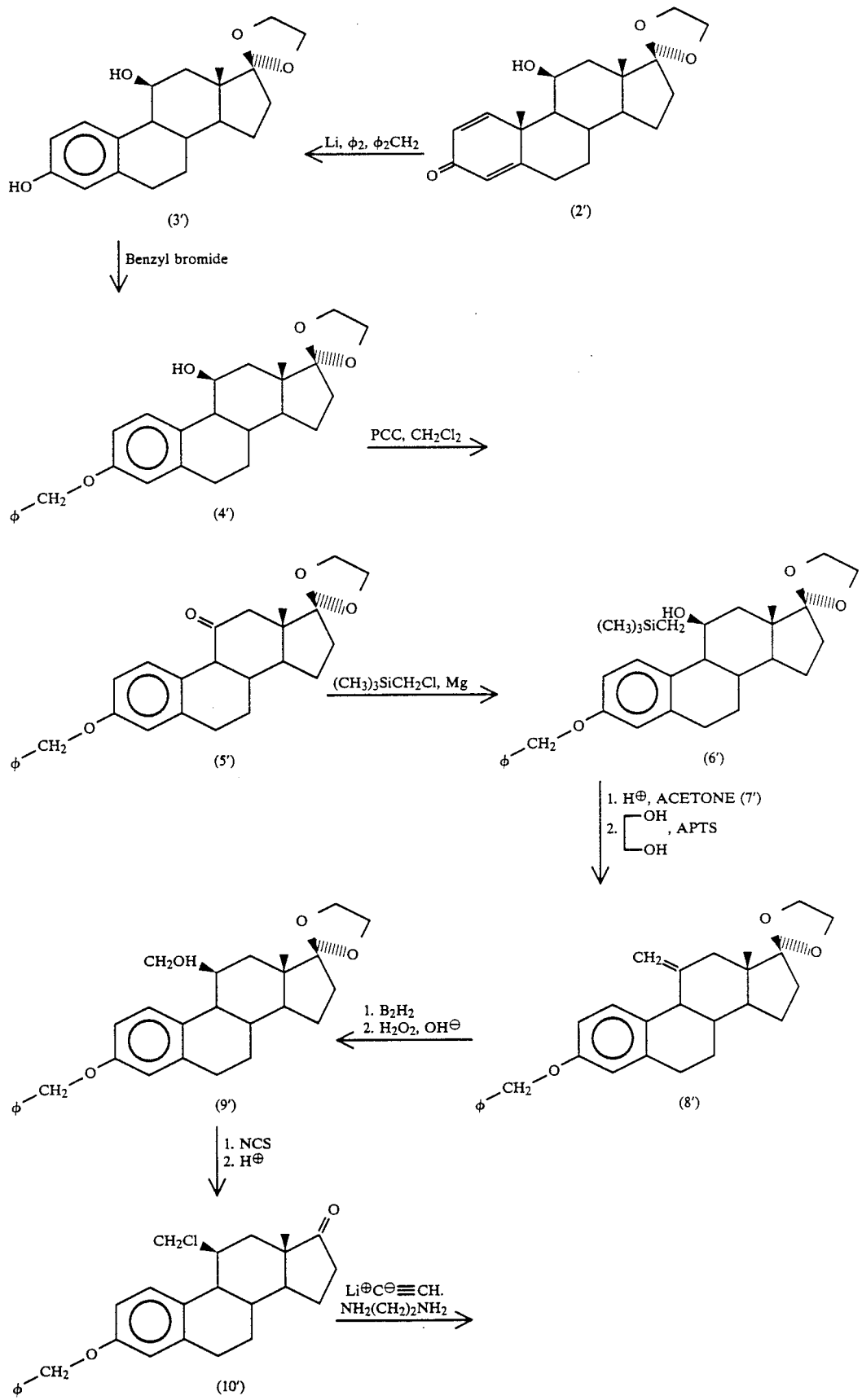

-continued
SCHEME 1

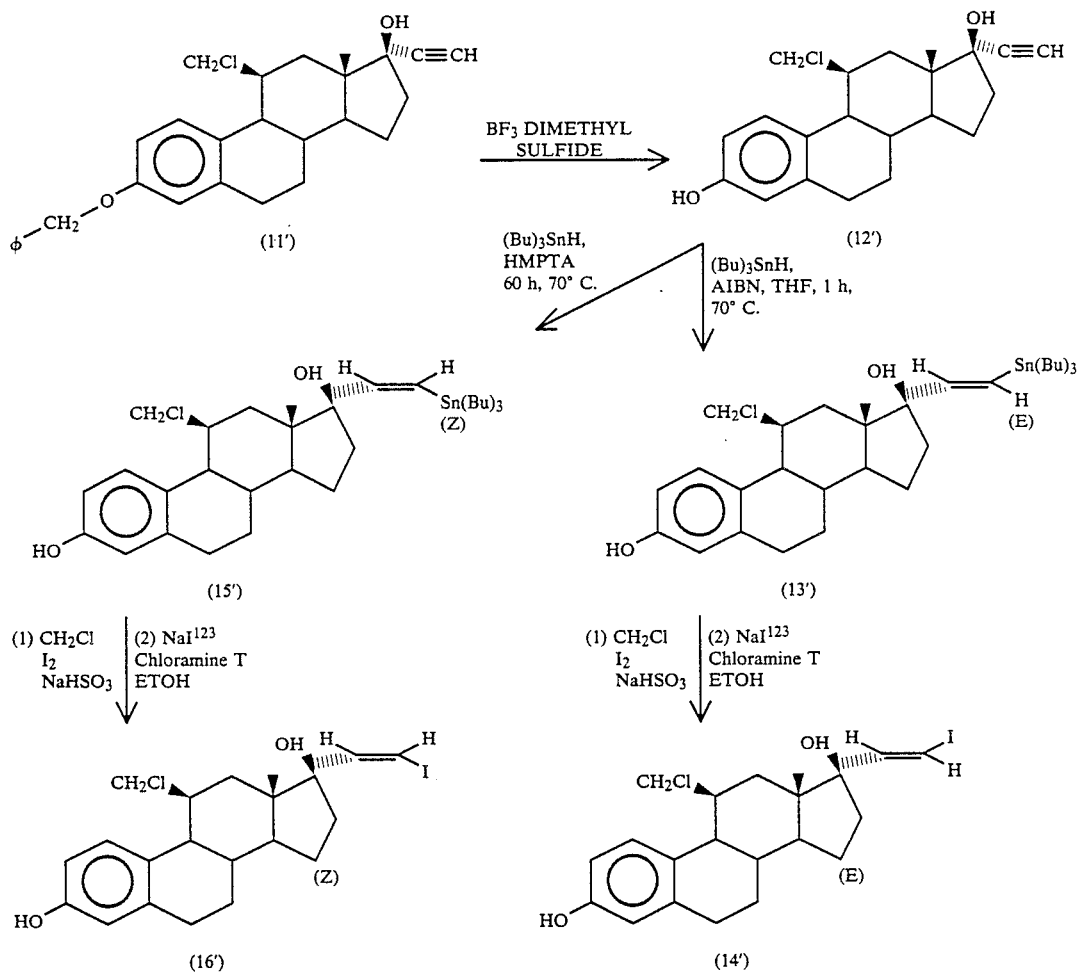

EXAMPLE 2

Biodistribution of the Z Isomer (16')

The biodistribution of the Z isomer (16') in ovarectomized BDF mice is highly favorable.

8 ovarectomized BDF1 mice were injected with 1 μCi of 11beta-chloromethyl-17alpha-(2-iodovinyl)estradiol-($^{125}$I). 4 mice were sacrificed 2 hours after the estradiolinjection and 4 24 hours after the injection. The percentages of injected doses per gram of tissue are given in Table 1 and shown in FIG. 1.

It is remarkable that the uterus/blood, uterus/fat and uterus/liver concentration ratios at 24 hours (shown in Table 2 below and in FIG. 1) should be far higher than those described in the literature for other steroids (for example in Hanson et al., Synthesis and Biodistribution of I-125 17-iodovinyl-11-ethylestradiol, in 7th International Symposium on Radiopharmaceutical Chemistry, Groningen, Netherlands, July 4–8, 1988; in normal immature female rats at 24 hours, the ratios given are:

uterus/liver=3.89,
uterus/lung=52.8,
uterus/blood=40.4).

Apart from its interest to hormone radiotherapy, this steroid 16' is of great interest both as an imagery agent and as a reactant for the quantitative determinations of estrogen receptors.

TABLE 1

| | % injected dose/g of tissue (+S.D.) | |
|---|---|---|
| TISSUE | time: 2 hours | time: 24 hours |
| Blood | 1.08 ± 0.24 | 0.14 ± 0.02 |
| Uterus | 6.66 ± 0.91 | 9.21 ± 1.44 |
| Liver | 5.10 ± 0.72 | 0.91 ± 0.05 |
| Kidneys | 1.84 ± 0.27 | 0.20 ± 0.02 |
| Spleen | 0.97 ± 0.18 | 0.12 ± 0.01 |
| Fat | 2.29 ± 0.25 | 0.26 ± 0.09 |
| Muscle | 0.89 ± 0.07 | 0 10 ± 0.02 |

TABLE 2

| RATIO | TIME: 2 h | TIME: 24 h |
|---|---|---|
| Uterus/blood | 6.16 | 65.80 |
| Uterus/muscle | 7.48 | 92.10 |
| Uterus/liver | 1.30 | 10.12 |
| Uterus/fat | 2.90 | 35.42 |

EXAMPLE 3

Use of 11Beta-Chloromethyl-17-Iodovinylestradiol-$^{123}$I in Targeted Radiotherapy The inhibition of the fixation of tritiated estradiol on cytosols of MCF7 mammary human tumor rich in estrogen receptors shows that, at 25° C., 11beta-chloromethyl-17-iodovinylestradiol has an affinity comparable with that of 11beta-chloromethylestradiol and clearly superior to that of estradiol ("relative binding affinity" greater than 1,000).

Twenty nine female BDF1 mice were grafted with MXT syngenetic mammary tumors implanted subcutaneously. Fourteen mice received three intravenous injections of 100 µCi of 11beta-chloromethyl-17-iodovinyl- $^{123}$I of E isomerism at fortnightly intervals.

The 100 µCi of labeled hormone were injected diluted in 200 µl of solution containing 9 g/l NaCl, 5% ethanol and 1% of Tween 80. The fifteen control mice received 200 µl of the NaCl/ethanol/Tween solution on the same dates. No acute toxicity was detected in these two groups over a period of 60 days.

The group of mice treated with the radioactive hormone showed a significant slowing down of the tumor growth compared with the control group (lower than 45% of the average tumor growth on day 18). The treated group also exhibited a better survival.

These results demonstrate an in-vivo effect of a targeted hormone radiotherapy with the aid of isotopes which emit Auger electrons.

EXAMPLE 4

Advantage of the Iodine 125-Labeled and Cold Products (16') AND (14') (Quantitative Determination of Receptor in the Tumors)

Tests of binding of calf uterus cytosol to the estrogen receptor (25° C., 1 h) at a saturating dose of iodine 125-labeled hormone (16') (final 5 mM) show a binding of the same order as the tritiated estradiol (also at final 5 mM) with a higher sensitivity level, by virtue of the higher specific activity, and a much lower nonspecific binding level (23% of the nonspecific binding against 62% for the tritiated ligand). The nonspecific binding to the transport proteins is diminished by virtue of the presence of the 11-beta and 17-alpha groups.

These characteristics bring an improvement in the quantitative determination of the estrogen receptor in tumor tissues originating from clinical biopsies.

The cold analog (16') is needed for the estimation of the nonspecific level (excess of cold hormone) in quantitative determination of this type.

In addition, 16' forms a potential powerful agonist estrogen.

EXAMPLE 5

Synthesis of Halogenated Derivatives Via the Tributyltin Derivatives

The advantage of the tributyltin derivatives (15') and (13') and the progestagen group analogs is that the latter are key intermediates in the synthesis of steroids in which one of the end hydrogens of the 17alpha vinyl functional group is substituted by a halogen (F, Cl, Br, I, At) or another atom whose cationic form can replace the tributyltin functional group.

It is thus possible, in particular, to prepare new derivatives according to the invention which are of interest to imagery ($^{18}$F) or therapy ($^{80m}$Br or $^{211}$At).

The synthesis of fluoro derivatives (cold or $^{18}$F) is performed in the following way: the tributyltin derivative (10 µmol) in CFCl$_3$ at −78° C. is reacted with 0.1% F$_2$ ($^{19}$F or $^{18}$F) in N$_2$ (50 µmol) for 40 minutes. After being put through HPLC, the pure product is obtained.

In the case of the $^{80m}$Br or $^{211}$At derivatives, the labeled derivatives are obtained from Na$^{80m}$Br or Na$^{211}$At, respectively, reacted for 10 minutes with the tributyltin precursor in ethanol and an equal volume of a 2:1 (v/v) solution of 30% H$_2$O$_2$ and glacial acetic acid. After the addition of a bisulfite solution, the halogenated derivatives are extracted on SPe C$_{18}$ cartridge (1 ML, Baker) and then purified by HPLC (µBondapack C$_{18}$ with 50 to 60% of EtOH in H$_2$O as mobile phase).

EXAMPLE 6

Specific Ligand for Progestagen Receptor

The synthesis route to the (E) and (Z) 11beta-chloromethyl-17alpha-iodovinyl-17beta-hydroxy-19-nor-4-androsten-3-one derivatives ((29') and (27') respectively) is described in scheme 2 below. It involves a modification of the scheme 1 described above in the case of the specific ligands for estrogen receptors. The starting point is 3,11beta-dihydroxyestra-1,3,5(10)-trien-17-one-17ethylene ketal (3').

Stage 1' consists of the methylation in the C$_3$ position of (3') by the action of K$_2$CO$_3$ and CH$_3$I and heating under reflux for 24 hours in acetone.

Stage 2' consists of the oxidation in the C$_{11}$ position with pyridinium chlorochromate (PCC) using a process similar to that described in stage 5 of scheme 1.

Stage 3' consists of the preparation of the derivative which is silylated in the C$_{11}$ position with the magnesium derivative of methyltrimethylsilyl chloride using the method of stage 6 of scheme 1, followed by the acidic hydrolysis described in stage 7 of scheme 1, itself followed by the protection at C$_{17}$ by the action of ethylene glycol in an acidic medium as described in a similar way in stage 8 of scheme 1. The compound (20') is thus obtained.

Stage 4' consists of the preparation of a borane derivative attached to the carbon carried by C$_{11}$ and its oxidation with H$_2$O$_2$ in a basic medium to give the C$_{18}$hydroxymethyl derivative (21') using the method which is similar to stage 9 of scheme 1.

Stage 5' consists of the protection of the hydroxyl attached at C$_{11}$ with a tetrahydropyranyl functional group. The method of synthesis consists of the action of DHP (dihydropyran) in THF in the presence of para-toluenesulfonic acid at ambient temperature overnight. After evaporation of the solvents, the derivative (22') is extracted with CH$_2$Cl$_2$ after addition of H$_2$O.

Stage 6' consists of the reduction, by a Birch reaction, of the compound (22'), followed by acidification with HCl to release the alpha,beta-conjugated ketone of the derivative (23'); the functional group at C$_{11}$ is deprotected at the same time. The operating method is as follows: 0.75 g of lithium are dissolved in 75 ml of liquid NH$_3$; a dark-blue color is obtained. During the reduction, the temperature is maintained below −50° C. using a solid CO$_2$ bath. 3.1 g of the steroid (22') are added. The mixture is stirred for 1 h 30 min. Next, 50 ml of isopropanol and 20 ml of ethanol are added dropwise. The decoloration is complete. The temperature is slowly raised again to 22° C. and the NH$_3$ is allowed to evaporate overnight.

After extraction with CH$_2$Cl$_2$, approximately 3 g of a whitish mass are obtained. This is heated under reflux for 20 minutes in a mixture of 100 ml of CH$_3$OH and 30 ml of 10% HCl in H$_2$O. After extraction with CH$_2$Cl$_2$, 1.7 g of a yellowish solid are obtained. After chromatography on silica gel with 15% of acetone in CH$_2$Cl$_2$, a product is obtained which is pure according to TLC and NMR.

TLC: silica, CH$_2$Cl$_2$(85%) and acetone (15%) R$_f$=0.20

Silica, CH$_2$Cl$_2$ (95%) and methanol (5%) R$_f$=0.27.

Spectroscopic data:

NMR (CDCl$_3$, TMS); chemical shift (ppm) 0.95 (s, 13CH$_3$), 3.7 (m, CHOH), 3.95 (m, CHHOH), 5.85 (s, CH=C)

Stage 7′ consists of the chlorination of the carbon-containing functional group at C$_{11}$ with N-chlorosuccinimide using the method of stage 10 of scheme 1. The compound 24′ is obtained.

Chlorination of 11-hydroxymethyl-Δ$^4$-estren-3,17-dione:

1. A solution of 5.34 g (20 mM) of triphenylphosphine in 80 ml of dry THF is added under dry N$_2$ to a solution of 2.71 g (20 mM) of N-chlorosuccinimide in 80 ml of dry THF.

The suspension obtained is then added with vigorous stirring to a solution of 3.22 g (10 mM) of 11hydroxymethyl-Δ$^4$-estren-3,17-dione in 70 ml of dry THF.

The reaction is allowed to proceed under N$_2$ and at ambient temperature overnight.

2. After evaporation of the solvent, dilution in pure water and extraction with dichloromethane, 9.4 g of a brownish solid are isolated.

After a purification on a silica column, 2.5 g (8 mM) are obtained; yld: 80% of yellowish crystals. TLC SiO$_2$ 24 CH$_2$C$_2$/1 acetone and 1 cyclohexane/1 ethyl acetate.

Stage 8′ consists of the ethynylation of the alpha functional group at C$_{17}$ of the compound 24′ by the method using the lithium acetylide-ethylenediamine complex according to the method which is similar to stage 11 of scheme 1. The compound 25′ is obtained 1. Protection of the C═O in position 3 (3-enamine). 2.4 g of the compound obtained in stage 7′ are dissolved under N$_2$ in 24 ml of warm methanol, and 1 ml of pyrrolidine is added. Gentle refluxing is maintained for 30 min and the solution is then allowed to return to ambient temperature overnight. The crystals are filtered off and washed with methanol. 2.3 g (80% yield) of a yellowish gray product are obtained. TLC SiO$_2$ 9 CH$_2$Cl$_2$/1 MeOH.

2. Ethynylation of the C═O at 17 (gives 17

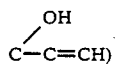

2.2 g of the compound obtained in stage 8′1. (56 mM) are dissolved under N$_2$ in 40 ml of DMSO. A solution of 3 g (30 mM) of the lithium acetylide-ethylenediamine complex in 20 ml of DMSO is added. After 2 h 30 min the reaction is stopped by being poured into a water/ice mixture. Extraction with ethyl acetate gives an orange-colored oil which is employed as such in the next stage.

3. Hydrolysis of the 3-enamine. The crude oil obtained above is redissolved in 50 ml of methanol. 2.5 ml of acetic acid, 2.5 g of sodium acetate and 6 ml of water are added to this solution.

The mixture is refluxed for 4 hours. The maximum quantity of solvent is then evaporated off and an extraction is carried out using a water-CH$_2$Cl$_2$ system. 2.2 g of a reddish oil are finally obtained.

4. The crude product is purified on a silica column. Eluent: 2% of acetone in dichloromethane.

0.6 g of slightly yellow crystals are obtained. Total yield: 30%. TCL SiO$_2$ 24 CH$_2$Cl$_2$/1 acetone, R$_f$=0.5.

Stage 9′ consists of the preparation of the (Z) tributyltin derivative (26′) by the method which is similar to that described in stage 15 of scheme 1.

Stage 10′ consists of the preparation of the derivative (Z)-11beta-chloromethyl-17beta-hydroxy-17alpha-(2-iodovinyl)-4-estren-3-one (27′).

When a cold iodine ($^{127}$I) is involved, the method of stage 16 of scheme 1 is employed, and when labeling with $^{123}$I or $^{125}$I is involved, the labeling method which is also described in scheme 1 is employed.

Stage 11′ consists of the preparation of the (E) tributyltin derivative (28′) using the method described in stage 13 of scheme 1.

Stage 12′ consists of the preparation of the derivative (E)-11beta-chloromethyl-17beta-hydroxy-17-alpha-(2-iodovinyl)-4-estren-3-one (29′).

When a cold iodine ($^{127}$I) is involved, the method of stage 14 of scheme 1 is employed, and when labeling with $^{123}$I or $^{125}$I is involved, the labeling method which is also described in connection with scheme 1 is employed.

SCHEME 2

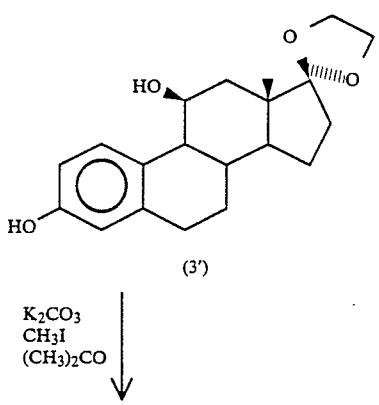

(3′)

K$_2$CO$_3$
CH$_3$I
(CH$_3$)$_2$CO

-continued
SCHEME 2
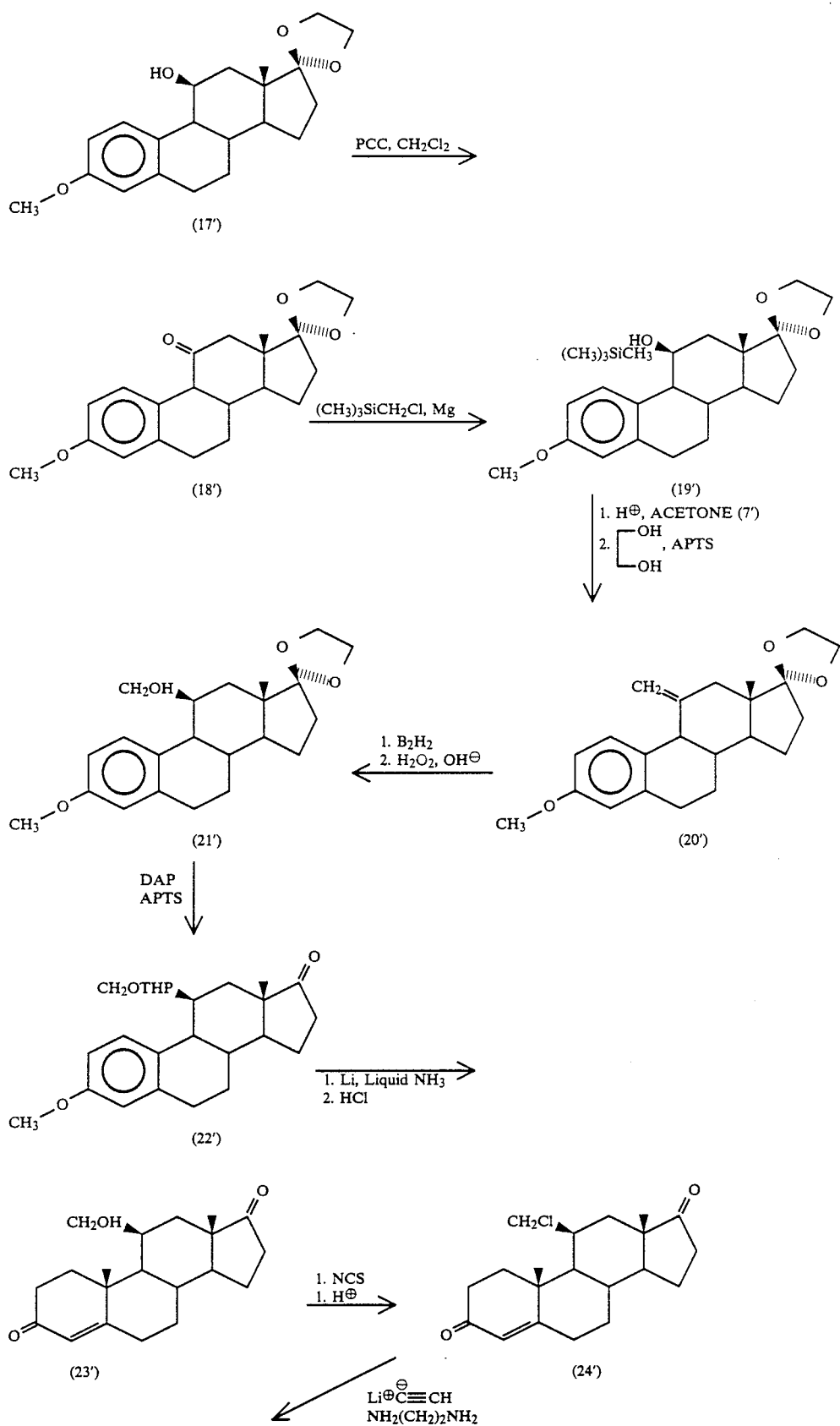

-continued
SCHEME 2

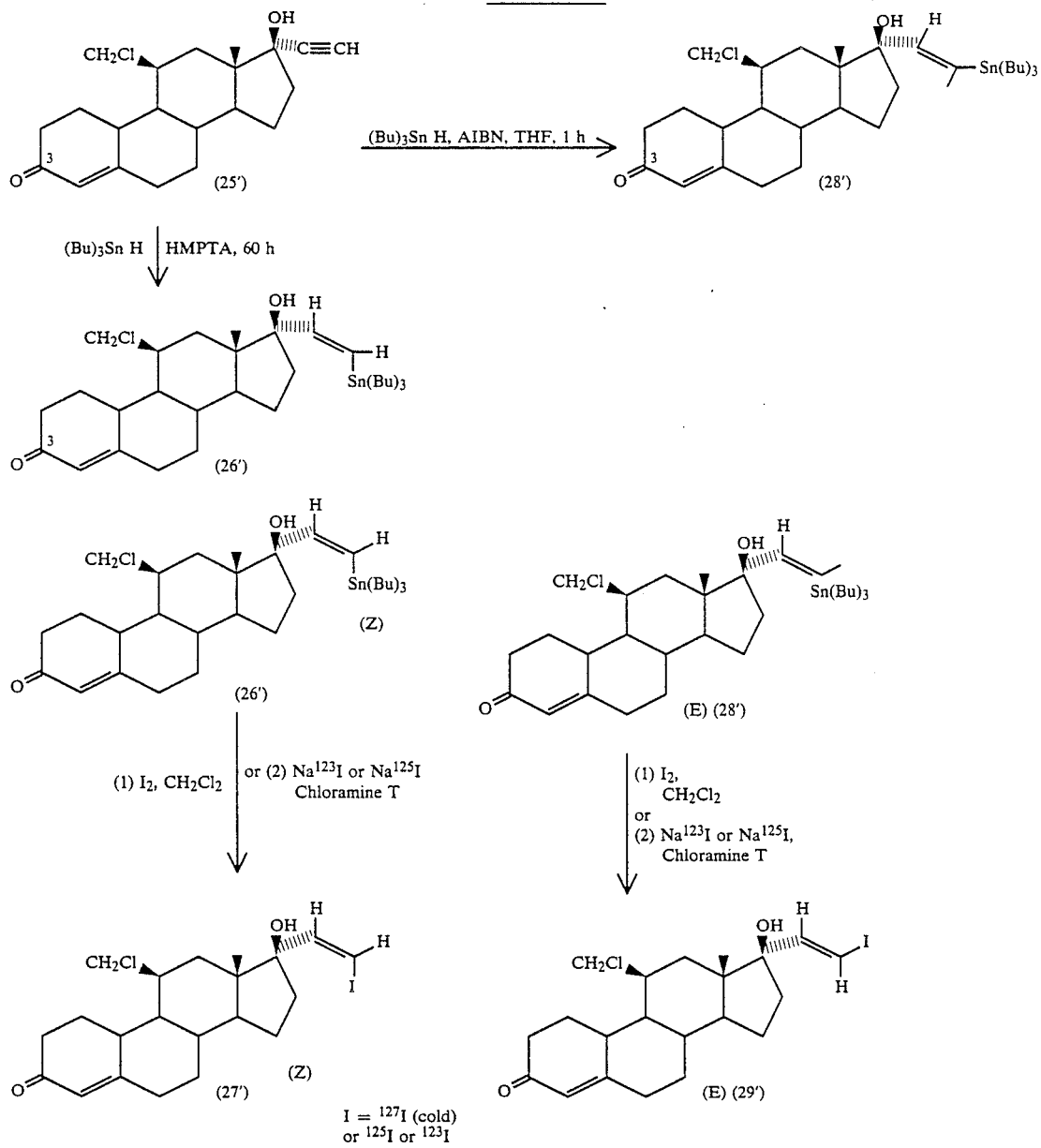

We claim:
1. Specific ligands for estrogen or progestagen steroid hormone receptors which have the formula

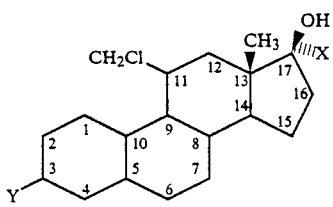   (I)

in which
X denotes a vinyl group substituted by a radioactive or nonradioactive halogen on the double bond according to a Z isomerism, and
Y denotes either a hydroxyl group, in which case the ring to which it is attached is an aromatic ring, or a ketone functional group, in which case it is conjugated with a double bond at $C_4$–$C_5$.

2. Specific ligands for steroid hormone receptors as claimed in claim 1, which can be used for the targeted therapy or the quantitative determination of said receptors, which contain a nonradioactive halogen chosen from iodine, fluorine, bromine and chlorine, substituted on the double bond of the alpha-oriented vinyl group attached to the $C_{17}$ position according to the Z isomerism of the double bond.

3. Specific ligands for steroid hormone receptors as claimed in claim 1, which can be used especially for the targeted therapy or imagery, especially of cancer, or the quantitative determination of said receptors, which contain a radioactive halogen chosen from the radioactive isotopes of fluorine, iodine, bromine and astatine, substituted on the double bond of the alpha-oriented vinyl group attached to the $C_{17}$ position according to the Z isomerism of the double bond.

4. Specific ligands for steroid hormone receptors as claimed in claim 3, which can be used especially for the targeted radiotherapy, especially of cancer, which contain a radioactive isotope chosen from $^{123}I$, $^{211}At$ and $^{80m}Br$ substituted on the double bond of the vinyl group, with alpha orientation in position $C_{17}$ according to the Z isomerism of the double bond.

5. Specific ligands for steroid hormone receptors as claimed in claim 3, which can be used especially for the medical imagery, especially of cancer, which contain a radioactive isotope chosen from $^{123}I$ and 18F.

6. Specific ligands as claimed in claim 3, which can be used especially for the quantitative determination of steroid hormone receptors, which contain the isotope $^{125}I$ substituted according to the Z isomerism on the double bond of the alpha-oriented vinyl group in the $C_{17}$ position.

7. Ligands as claimed in claim 1 wherein the functional group in position $C_3$ is a hydroxyl group attached to an aromatic ring.

8. Ligands as claimed in claim 1 wherein the functional group in position $C_3$ is a ketone functional group conjugated with a double bond at $C_4$-$C_5$.

9. Ligands as claimed in claim 8, which are an 11beta-chloromethyl-17alpha-halovinylestradiol.

10. Ligands as claimed in claim 8, which are an 11beta-chloromethyl-17alpha-halovinyl-17beta-hydroxy-19nor-4-androsten-3-one.

11. A ligand as claimed in claim 7, which is an 11beta-chloromethyl-17alpha-iodovinylestradiol of Z isomerism.

12. A ligand as claimed in claim 8, which is an 11beta-chloromethyl-17alpha-iodovinyl-17beta-hydroxy-19-nor-4-androsten-3-one of Z isomerism.

13. As a new product which can be used especially in the synthesis of specific ligands as claimed in one of the preceding claims, a product of formula

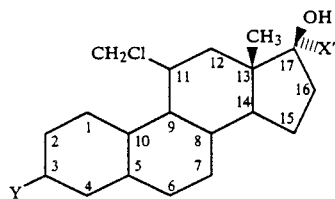

(I)

in which
X' denotes an alpha-oriented vinyl group in the $C_{17}$ position on the double bond of which a tributylstannyl group is substituted as claimed in a Z isomerism, and denotes either a hydroxyl group, in which case the ring to which it is attached is an aromatic ring, or a ketone functional group, in which case it is conjugated with a double bond at $C_4$-$C_5$.

14. In a process for the synthesis of a ligand having the formula

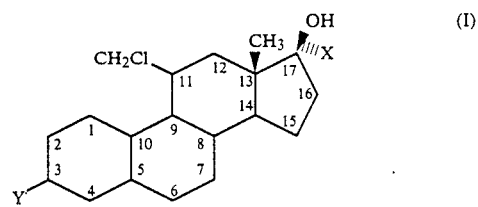

(I)

in which
X denotes a vinyl group substituted by a radioactive or nonradioactive halogen on the double bond according to the Z isomerism, and
Y denotes either a hydroxyl group, in which case the ring to which it is attached is an aromatic ring, or a ketone functional group, in which case it is conjugated with a double bond at $C_4$-$C_5$,
the improvement which comprises employing a halogenated derivative of a ligand with the formula

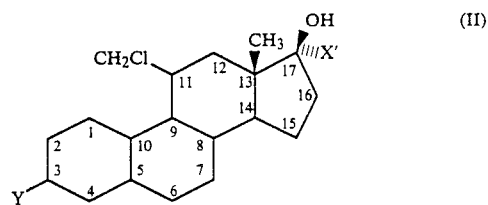

(II)

in which
X' denotes an alpha-oriented vinyl group in the $C_{17}$ position on the double bond of which a tributylstannyl group is substituted as claimed in a Z isomerism, and denotes either a hydroxyl group, in which case the ring to which it is attached is an aromatic ring, or a ketone functional group, in which case it is conjugated with a double bond at $C_4$-$C_5$.

* * * * *